United States Patent [19]
Cakara et al.

[11] 4,160,783
[45] Jul. 10, 1979

[54] 4-DEDIMETHYLAMINO-4-ARYLSUL-FONAMIDO-5A,6-ANHYDROTETRACY-CLINES

[75] Inventors: Marica Čakara; Slobodan Djokić; Zrinka Tamburašev, all of Zagreb, Yugoslavia

[73] Assignee: PLIVA Pharmaceutical and Chemical Works, Yugoslavia

[21] Appl. No.: 855,496

[22] Filed: Nov. 28, 1977

[30] Foreign Application Priority Data

Nov. 26, 1976 [YU] Yugoslavia .................... 2901/76

[51] Int. Cl.$^2$ .................... C07C 143/79; A61K 31/18
[52] U.S. Cl. .................... 260/556 AR; 260/556 B; 260/559 AT; 424/321
[58] Field of Search ..... 260/556 AR, 556 B, 559 AT, 260/371

[56] References Cited

U.S. PATENT DOCUMENTS

| | | | |
|---|---|---|---|
| 3,265,732 | 8/1966 | Miller et al. | 260/556 AR X |
| 3,828,040 | 8/1974 | Bien et al. | 260/371 X |
| 3,914,299 | 10/1975 | Muxfeldt | 260/559 AT |
| 4,013,621 | 3/1977 | Knell | 260/556 AR X |
| 4,032,518 | 6/1977 | Kotlarchik, Jr. et al. | 260/556 AR X |

Primary Examiner—Thomas Waltz
Attorney, Agent, or Firm—Pollock, Vande Sande & Priddy

[57] ABSTRACT

Novel 4-dedimethylamino-4-arylsulfonamido-5a,6-anhydrotetracyclines of the general formula I

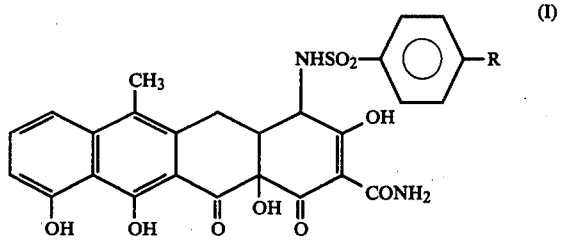

(I)

wherein R stands for $C_1$-$C_3$-alkyl, halogen or —NHCOR$^1$, $R^1$ being $C_1$-$C_3$-alkyl.

10 Claims, No Drawings

4-DEDIMETHYLAMINO-4-ARYLSULFONAMIDO-5A,6-ANHYDROTETRACYCLINES

The invention concerns new 4-dedimethylamino-4-arylsulfonamido-5a,6-anhydrotetracyclines (hereafter referred to as 4-arylsulfonamido-5a,6-anhydrotetracyclines) of the general formula I

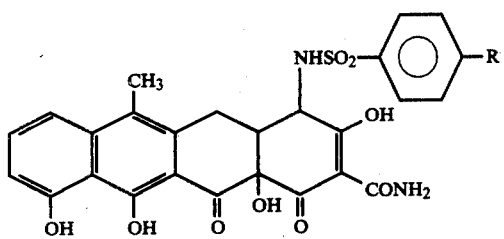

wherein R stands for $C_1$–$C_3$-alkyl, halogen or —NHCOR[1], R[1] being $C_1$–$C_3$-alkyl, which are prepared by reacting 4-dedimethylamino-4-aminotetracycline (4-aminotetracycline) with arylsulfochlorides and then dehydrating the obtained products, or reacting 4-dedimethylamino-4-amino-5a,6-anhydrotetracyclines (4-amino-5a,6-anhydrotetracyclines) with arylsulfochlorides.

It has been known to prepare 4-dedimethylamino-4-amino-5a,6-anhydrotetracycline derivatives of the general formula II

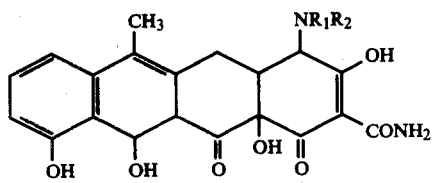

wherein $R_1$ can represent hydrogen, benzyl, phenetyl, cyclohexyl or $C_2$–$C_6$-alkyl and $R_2$ can represent hydrogen, $C_2$–$C_6$-alkyl or $C_2$–$C_4$-hydroxyalkyl, by reacting the corresponding alkyliodides with 4-amino-5a,6-anhydrotetracycline in the presence of propylene oxide (U.S. Pat. No. 3,622,627).

It has been found that 4-arylsulfonamido-5a,6-anhydrotetracyclines can be prepared by reacting 4-aminotetracycline with excess arylsulfochloride in an appropriate solvent (acetone) in the presence of an alkaline agent, such as sodium hydrogencarbonate, at elevated temperatures, followed by dehydration of the obtained products by refluxing in a dilute mineral acid solution. It has also been found that the same compounds can be prepared by reacting the corresponding 4-amino-5a,6-anhydrotetracyclines with excess arylsulfochloride in an appropriate solvent (e.g. acetone) in the presence of an alkaline agent, e.g. sodium hydrogencarbonate, at elevated temperatures. In this case, however, the yields are somewhat lower.

The tests of antibacterial activity of some compounds according to the present invention against Gram-positive and Gram-negative microorganisms compared with the known antimicrobial activity of tetracycline and 4-amino-5a,6-anhydrotetracycline are shown in Table 1.

TABLE 1

| Microorganism tested | MIC in mcg for the compounds | | | | | | |
|---|---|---|---|---|---|---|---|
| | 1 | 2 | 3 | 4 | 5 | 6 | 7 |
| *Streptococcus faecalis* ATCC 8043 | 0.5 | 20 | 50 | 5 | 100 | 5 | 50 |
| *Staphylococcus aureus* ATCC 6538-P | 0.5 | 10 | 5 | 1 | 100 | 10 | 10 |
| *Staphylococcus epidermidis* ATCC 12228 | 100 | 0.5 | 5 | 0.5 | 100 | 0.5 | 10 |
| *Micrococcus flavus* ATCC 10240 | 0.5 | 0.1 | 0.5 | 0.5 | 50 | 0.5 | 5 |
| *Sarcina lutea* ATCC 9341 | 0.5 | 0.5 | 5 | 0.5 | 50 | 5 | 5 |
| *Bacillus cereus* var. mycoides ATCC 11778 | 0.5 | 20 | 50 | 100 | 100 | 100 | 20 |
| *Bacillus subtilis* ATCC 6633 | 0.5 | 1 | 20 | 0.5 | 100 | 20 | 5 |

1 tetracycline hydrochloride
2 4-p-toluene-sulfonamido-5a,6-anhydrotetracycline
3 4-p-fluorbenzenesulfonamido-5a,6-anhydrotetracycline
4 4-p-bromobenzenesulfonamido-5a,6-anhydrotetracycline
5 4-p-acetylaminobenzenesulfonamido-5a,6-anhydrotetracycline
6 4-p-ethylbenzenesulfonamido-5a,6-anhydrotetracycline
7 4-amino-5a,6-anhydrotetracycline It is evident from the Table that all compounds tested show a significant activity in the test against microorganisms. Particularly active are the compounds Nos. 2, 3, 4 and 6 which display the strongest activity against Micrococcus flavus ATCC 10240, Sarcina lutea ATCC 9341 and Staph. epidermidis ATCC 12228, their activity being considerably superior or equal to that of tetracycline.

The invention is illustrated by the following Examples.

EXAMPLE 1

Preparation of 4-dedimethylamino-4-p-toluenesulfonamido-5a,6-anhydrotetracycline 4-Dedimethylamino-4-aminotetracycline (hereafter referred to as 4-aminotetracycline) (1 mmole) is suspended in acetone (15 ml.). To this suspension there is added under stirring p-toluenesulfochloride (1.2 mmoles) and then dropwise a solution of sodium hydrogencarbonate (2.4 mmoles) in water (5 ml.). The suspension is gently refluxed for one hour, whereby a clear, somewhat darker solution is obtained. Acetone is evaporated from the solution under reduced pressure, water (20 ml.) is added to the residue and the mixture is homogenized by stirring. The pH of the mixture is 8.2. Sideproducts are removed by filtration and concentrated hydrochloric acid is added to the clear filtrate so as to adjust the pH to 1.8, whereby an abundant light yellow precipitate separates, which is filtered after stirring for 10 minutes, resuspended in water (50 ml.), filtered again, washed and air-dried. There are obtained 0.39 g. (68.5%) of 4-p-toluenesulfonamidotetracycline. The product is identified by elementary analysis, TLC, UV, IR, NMR and mass spectra. The obtained compound (1.76 mmoles) is dissolved in a mixture of methanol (80 ml.) and concentrated hydrochloric acid (2 ml.) and the solution is refluxed for two hours, then it is filtered and the filtrate is evaporated to dryness under reduced pressure. The orange coloured residue is suspended in water (50 ml.), stirred for 10 min. and filtered. The precipitate is resuspended in water (50 ml.), stirred for 10 min., filtered, washed with water until the test on chlorides in the filtrate is negative and dried to constant weight. Yield: 1 g. (100%). M.p. 198°–224° C. (decomp.).

$C_{27}H_{24}N_2O_9S.H_2O$: C, 56.86; H, 4.56; N, 4.91; S, 5.62%. Found: C, 57.06; H, 4.62; N, 4.83; S, 5.93%.

| | |
|---|---|
| MeOH-0.01 N HCl $\lambda$max | 270 and 420 m/$\mu$ |
| MeOH-0.01 N NaOH $\lambda$max | 269 and 420 m/$\mu$ |

EXAMPLE 2

Preparation of 4-dedimethylamino-4-p-ethylbenzenesulfonamido-5a,6-anhydrotetracycline 4-Aminotetracycline (2 mmoles) and p-ethylbenzenesulfochloride (2.1 mmoles) are suspended in acetone (15 ml.) and a solution of sodium hydrogencarbonate (4.2 mmoles) in water (10 ml.) is added dropwise under stirring. The reaction mixture is stirred at ambient temperature for two hours, wheby an almost clear solution is obtained. The solution is then filtered, acetone is evaporated from the filtrate under reduced pressure and water (40 ml.) is added to the residue. The mixture is homogenized, filtered and the precipitate is washed with water (10 ml.). Thus there are obtained 0.52 g. of the air-dried product. In the filtrate, pH is adjusted from 7.8 to 1.8 by the dropwise addition of concentrated hydrochloric acid, the thus formed precipitate is stirred for 10 minutes, filtered and treated with water according to Example 1. There are obtained further 0.45 g. The overall yield (0.97 g.) of 4-dedimethylamino-4-p-ethylbenzenesulfonamidotetracycline is 83%. From this compound, according to the procedure as described in Example 1, there is prepared 4-p-ethylbenzenesulfonamido-5a,6-anhydrotetracycline in a yield of 100%. M.p. 163°–175° C. (decomp.).

$C_{28}H_{26}N_2O_9S.H_2O$: C, 57.55; H, 4.79; N, 4.79; S, 5.48%. Found: C, 57.52; H, 4.86; N, 4.88; S, 5.94%.

EXAMPLE 3

Preparation of 4-dedimethylamino-4-p-bromobenzenesulfonamido-5a,6-anhydrotetracycline 4-Aminotetracycline (2 mmoles) and bromobenzenesulfochloride are suspended in acetone (20 ml.) and a solution of sodium hydrogencarbonate (4.8 mmoles) in water (10 ml.) is added dropwise under stirring. The reaction mixture is stirred at ambient temperature for two hours, filtered, acetone is evaporated from the filtrate and the residue is homogenized with water (45 ml.). The suspension is stirred for 10 minutes, filtered, the pH of the filtrate is adjusted to 1.8 by addition of concentrated hydrochloric acid. After short stirring the lightly coloured precipitate is filtered and treated with water according to Example 1. There are obtained 0.95 g. (74.8%) of 4-dedimethylamino-4-p-bromobenzenesulfonamidotetracycline which is converted to 4-p-bromobenzenesulfonamido-5a,6-anhydrotetracycline according to the procedures as described in Example 1 in a 100% yield. M.p. 205°–212° C. (decomp.).

$C_{26}H_{21}BrN_2O_9S.H_2O$: C, 49.15; H, 3.62; N, 4.41; S, 5.04%. Found: C, 49.37; H, 3.56; N, 4.12; S, 4.98%.

EXAMPLE 4

Preparation of 4-dedimethylamino-4-p-fluorobenzenesulfonamido-5a,6-anhydrotetracycline 4-p-Fluorobenzenesulfonamidotetracycline is obtained in a 70.5% yield by reacting 4-aminotetracycline (2 mmoles), p-fluorobenzenesulfochloride (2.4 mmoles) and sodium hydrogencarbonate (4.8 mmoles) according to the procedure as described in Example 3. From this compound 4-p-fluorobenzenesulfonamido-5a,6-anhydrotetracycline is prepared in a 88% yield by the procedure as described in Example 1. M.p. 210°–214° C. (decomp.).

$C_{26}H_{21}FN_2O_9S.H_2O$: C, 54.50; H, 4.01; N, 4.88; S, 5.58%. Found: C, 54.40; H, 3.79; N, 5.50; S, 5.18%.

EXAMPLE 5

Preparation of 4-dedimethylamino-4-p-acetylaminobenzenesulfonamido-5a,6-anhydrotetracycline By the procedure as described in Example 3, from 4-aminotetracycline (2 mmoles), acetylaminobenzenesulfochloride (2.2 mmoles) and sodium hydrogencarbonate (4.4 mmoles) there are obtained 0.90 g. (73.4%) of 4-p-acetylaminobenzenesulfonamidotetracycline, which, by the procedure as described in Example 1, is converted to 4-p-acetylaminobenzenesulfonamido-5a,6-anhydrotetracycline in a 84% yield. M.p. 190°–230° C. (decomp.).

$C_{28}H_{25}N_3O_{10}S.H_2O$: C, 54.8; H, 4.40; N, 6.85; S, 5.22%. Found: C, 54.73; H, 4.07; N, 6.61; S, 5.36%.

EXAMPLE 6

Preparation of 4-dedimethylamino-4-p-propionylaminobenzenesulfonamido-5a,6-anhydrotetracycline By the procedure as described in Example 3, there are obtained 4.06 g. (71.3%) of 4-p-propionylaminobenzenesulfonamidotetracycline from 4-amino-tetracycline (1 mmole), p-propionylaminobenzenesulfochloride (1.2 mmoles) and sodium hydrogencarbonate (2.4 mmoles). From this compound 4-p-propionylaminobenzenesulfonamido-5a,6-anhydrotetracycline is obtained in a 81.7% yield, according to the procedure as described in Example 1. M.p. 195°–212° C. (decomp.).

$C_{29}H_{27}N_3O_{10}S$: C, 55.5; H, 4.62; N, 6.7; S, 5.1%. Found: C, 55.28; H, 4.85; N, 6.48; S, 5.85%.

EXAMPLE 7

Preparation of 4-dedimethylamino-4-p-toluenesulfonamido-5a,6-anhydrotetracycline from 4-dedimethylamino-4-amino-5a,6-anhydrotetracycline 4-Amino-5a,6-anhydrotetracycline (1 mmole) and p-toluenesulfochloride (1.2 mmoles) are suspended in acetone (20 ml.) and to this suspension a solution of sodium hydrogencarbonate (3.6 mmoles) in water (7 ml.) is added. The reaction mixture is stirred at ambient temperature for two hours, the unreacted 4-amino-5a,6-anhydrotetracycline (0.23 g.=55%) is filtered off, acetone is evaporated from the filtrate and the residue is homogenized with water (25 ml.). The undissolved matter is filtered off, the pH of the filtrate is adjusted to 2.2 by the addition of concentrated hydrochloric acid and the formed precipitate is filtered and treated with water according to Example 1. Thus there are obtained 0.05 g. (8.9%) of 4-p-toluenesulfonamido-5a,6-anhydrotetracycline, which is identical with the product obtained in Example 1.

EXAMPLE 8

Preparation of 4-dedimethylamino-4-p-acetylaminobenzensulfonamido-5a,6-anhydrotetracycline from 4-dedimethylamino-4-amino-5a,6-anhydrotetracycline By the procedure as described in Example 7, from 4-amino-5a,6-anhydrotetracycline (0.5 mmoles), p-acetylaminobenzenesulfochloride (0.6 mmoles) and sodium hydrogencarbonate (1.2 mmoles) there are obtained 0.03 g. (9.8%) of 4-p-acetylaminobenzenesulfonamido-5a,6-anhydrotetracycline, which is identical with the product as obtained in Example 5.

What is claimed is:

1. A 4-dedimethylamino-4-arylsulfonamido-5a,6-anhydrotetracycline of the formula I

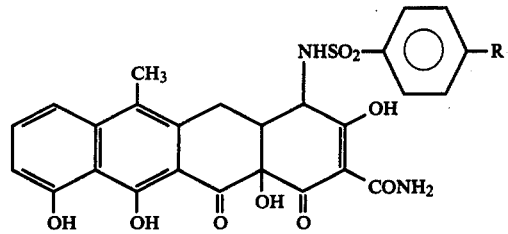

wherein R stands for $C_1$-$C_3$-alkyl, halogen or —NHCOR$^1$, and R$^1$ being $C_1$-$C_3$-alkyl.

2. The 4-dedimethylamino-4-arylsulfonamide-5a,6-anhydrotetracycline of claim 1 wherein R is a halogen.

3. The 4-dedimethylamino-4-arylsulfonamido-5a,6-anhydrotetracycline of claim 1 wherein R stands for —NHCOR$^1$, R$^1$ being $C_1$-$C_3$-alkyl.

4. The 4-dedimethylamino-4-arylsulfonamido-5a,6-anhydrotetracycline of claim 1 wherein R stands for $C_1$-$C_3$-alkyl.

5. The 4-dedimethylamino-4-arylsulfonamido-5a,6-anhydrotetracycline of claim 1 wherein R is methyl.

6. The 4-dedimethylamino-4-arylsulfonamido-5a,6-anhydrotetracycline of claim 1 wherein R is ethyl.

7. The 4-dedimethylamino-4-arylsulfonamido-5a,6-anhydrotetracycline of claim 1 wherein R is bromo.

8. The 4-dedimethylamino-4-arylsulfonamido-5a,6-anhydrotetracycline of claim 1 wherein R is fluoro.

9. The 4-dedimethylamino-4-arylsulfonamido-5a,6-anhydrotetracycline of claim 1 wherein R is propionylamino.

10. The 4-dedimethylamino-4-arylsulfonamido-5a,6-anhydrotetracycline of claim 1 wherein R is acetylamino.

* * * * *